United States Patent
Anderson

[11] Patent Number: 5,347,065
[45] Date of Patent: Sep. 13, 1994

[54] ALKYLATION CATALYST REGENERATION

[75] Inventor: Richard L. Anderson, Bartlesville, Okla.

[73] Assignee: Phillips Petroleum Company, Bartlesville, Okla.

[21] Appl. No.: 51,916

[22] Filed: Apr. 26, 1993

[51] Int. Cl.$^5$ .............................................. C07C 2/62
[52] U.S. Cl. ...................................... 585/724; 585/719; 585/723
[58] Field of Search ................ 585/719, 704, 724, 723

[56] References Cited

U.S. PATENT DOCUMENTS

| | | | |
|---|---|---|---|
| 3,749,753 | 7/1973 | Skraba | 585/724 |
| 3,795,712 | 3/1974 | Torch et al. | 260/671 C |
| 4,316,998 | 2/1982 | Van Pool | 585/723 |
| 4,404,418 | 9/9198 | Hulson, Jr. et al. | 585/723 |
| 4,513,165 | 4/1985 | Van Pool | 585/723 |
| 5,191,150 | 3/1993 | Child et al. | 585/724 |
| 5,237,122 | 8/1993 | Eastman et al. | 585/724 |

Primary Examiner—Asok Pal
Attorney, Agent, or Firm—Charles W. Stewart

[57] ABSTRACT

Disclosed is an alkylation process which ultilizes a mixture of sulfolane and hydrogen fluoride as an alkylation catalyst. The process provides for the removal of water from the alkylation catalyst that accumulates within the alkylation process system as a result of the incoming water which accompanies the catalyst mixture make-up components.

8 Claims, 1 Drawing Sheet

ALKYLATION CATALYST REGENERATION

The present invention relates to a hydrocarbon conversion process. More particularly, tile invention relates to a process for the alkylation of olefin hydrocarbons by isoparaffin hydrocarbons which utilizes a catalyst mixture comprising a sulfone compound, a hydrogen halide compound and water.

BACKGROUND OF THE INVENTION

It has recently been discovered that a mixture, comprising a sulfone compound and a hydrogen halide compound, can be an effective catalyst for use in the alkylation of olefin hydrocarbons by isoparaffin hydrocarbons to produce an alkylate reaction product, or alkylate. The alkylate reaction product generally contains hydrocarbons having seven or more carbon atoms, and it is a highly desirable gasoline blending component because of its high octane value as a motor fuel.

While a process which utilizes a catalyst composition comprising a sulfone component and a hydrogen halide component produces an alkylate product of very high quality, one side effect from using such a process in the production of alkylate is the formation of certain polymeric reaction by-products such as those referred to as acid-soluble oils, or ASO. These polymeric reaction by-products are referred to as acid-soluble oils because they are soluble in the catalyst utilized in the alkylation process and, thus, remain in the catalyst phase when the alkylate product resulting from the contact of a hydrocarbon mixture with an alkylation catalyst is separated from the alkylation catalyst. In an alkylation process which continuously separates the catalyst phase from the alkylation reaction product for reuse in the process reaction zone, there is a buildup of ASO in the catalyst. Over time, the ASO concentration will reach unacceptable concentration levels if not removed. A low concentration of ASO in the alkylation catalyst comprising a sulfone component and a hydrogen halide component is believed to have a beneficial effect upon the alkylation process or its product. However, higher concentrations of ASO in the alkylation catalyst have an adverse effect upon the catalyst activity and the final alkylate end-product. An ASO concentration in the alkylation catalyst that exceeds certain acceptable limits will result in lowering the octane of the alkylate end-product with incremental increases in the ASO concentration causing incremental decreases in-the alkylate octane.

In a continuous alkylation process which uses a catalyst having a sulfolane component and a hydrogen fluoride component, there can be an undesirable accumulation over time of water within the catalyst. This accumulation can result from the water that is contained within an alkylation feed, but it primarily results from the addition of the make-up catalyst components which generally contain concentrations of water. Particularly, the make-up sulfolane component of an alkylation catalyst often contains a significant concentration of water which, as has recently been discovered, will accumulate with:[.n the catalyst phase contained in the alkylation process system. While a small concentration of water within the alkylation catalyst phase may provide certain benefits, a too high concentration of water can have detrimental affects upon the alkylation process and its products. Thus, it is important for an alkylation process which uses a catalyst comprising sulfolane and hydrogen fluoride to have the ability to control the concentration of water contained in the catalyst.

In conventional alkylation processes that use a substantially pure hydrogen fluoride (tF) material as a catalyst, as opposed to the use of the aforementioned catalyst mixture comprising a sulfone component and a hydrogen halide component, there are certain known methods used to remove the ASO and water from the tIF catalyst used in a continuous alkylation process. Particularly, enough of a portion of the HF catalyst that is utilized in the conventional alkylation process is treated, or regenerated, so as to remove an amount of ASO and water at a rate that approximates the rate of accumulation of ASO and water in the alkylation catalyst. This is done by passing a portion of the HF catalyst to s stripping vessel, whereby the HF is stripped from the ASO by means of a vaporous hydrocarbon such as isobutane. The HF passes as a part of the vaporous overhead stream from the stripping vessel, and the ASO and water passes as a bottoms stream from the stripping vessel for further processing.

While the conventional alkylation catalyst regeneration techniques have worked well in the regeneration of the conventional HF catalyst, conventional means cannot be used -to regenerate an alkylation catalyst mixture which includes a sulfone component. This is because the boiling range of ASO overlaps the boiling temperatures of certain sulfones such as sulfolane. Also, the azeotropic properties of water and hydrogen fluoride impact the ability to separate water from the sulfolane and hydrogen fluoride catalyst. Therefore, simple distillation or stripping techniques as are used to separate HF from ASO cannot be used to effectively regenerate a sulfone-containing alkylation catalyst. Additionally, it is necessary to separate ASO from the sulfone in order to reclaim it for reuse as a catalyst in the alkylaltion process.

SUMMARY OF THE INVENTION

It is therefore an object of this invention to provide a novel alkylation process which can utilize a sulfolane and hydrogen fluoride mixture as an alkylation catalyst.

A further object of this invention is to provide an alkylation process which permits the removal of ASO and water from the alkylation catalyst containing a sulfone component.

A still further object ozf this invention is to provide an alkylation process that uses a sulfolane and hydrogen fluoride mixture as a catalyst and that provides a method by which any accumulation of ASO, water, or both, within the catalyst can be removed.

Thus, the process of the present invention relates to the alkylation of olefin hydrocarbons by paraffin hydrocarbons by utilizing a catalyst mixture that includes a sulfone component. The process includes mixing sulfolane having a concentration of water with HF to form a catalyst mixture, comprising sulfolane, water and tIF. The mixing step is followed by contacting a hydrocarbon mixture, comprising olefins and isoparaffins, with said catalyst mixture within a reaction zone to thereby produce a reaction product and a reaction by-product. The reaction product is separated from the catalyst mixture within a first separation zone to produce a separated reaction product and a separated catalyst mixture with the separated catalyst mixture containing a portion of the reaction by-product. A portion of the separated catalyst mixture is passed to a second separation zone to thereby separate -the portion of the separated catalyst mixture into a second separation zone overhead stream, comprising a portion of the ttF component of the portion of said separated catalyst mixture and a portion of the water component of the portion of the separated catalyst mixture, and a second separation zone bottoms stream, comprising a portion of the sulfolane component of the portion of the separated catalyst mixture and a portion of the :reaction by-product component of the portion of the separated catalyst mixture. A remaining portion of the separated catalyst mixture is utilized as a portion of the catalyst mixture. The second separation zone overhead stream is condensed to produce a condensed second separation zone overhead stream, with a portion of the condensed second separation zone overhead stream being utilized as a portion of the catalyst mixture. The remaining portion of the condensed second separation zone overhead stream is passed to downstream processing at a rate which is effective in maintaining a concentration of water in the separated catalyst mixture below about 10 weight percent.

BRIEF DESCRIPTION OF THE DRAWING

The accompanying FIG, 1 provides schematic representation of the process which is one embodiment of the invention, Other objects and advantages of the invention will be apparent from the foregoing detailed description of the invent]on and the appended claims.

DETAILED DESCRIPTION OF THE INVENTION

Figure 1:
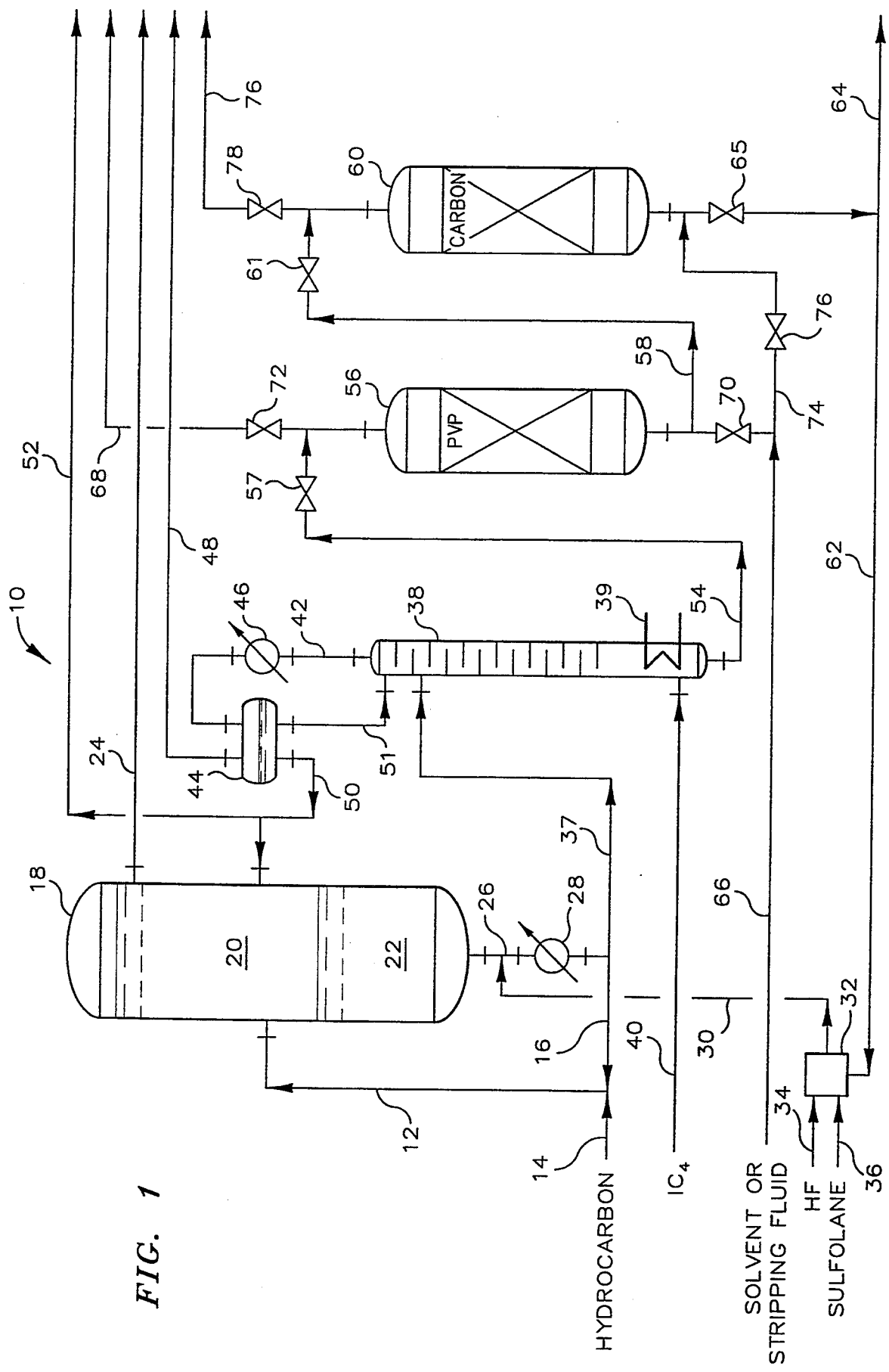

The acid soluble oil referred to herein is produced as a reaction by-product in an alkylation process comprising the step of contacting a hydrocarbon mixture, which comprises olefins and isoparaffins, with an alkylation catalyst, which comprises a hydrogen halide component and a sulfone component. As used within this description and in the appended claims, the term "acid soluble oil", or "ASO", means those conjunct polymers which are highly olefenic oils produced by acid-catalyzed reactions of hydrocarbons. An extensive description and characterization of certain types of conjunct polymer oils is provided in the *Journal of Chemical and Engineering Data* article entitled "Molecular Structure of Conjunct Polymers", pages 150–160, Volume 8, Number 1., (January 1963) by Miron and Lee. This article is incorporated herein by reference. The physical properties of ASO depend upon the particular hydrocarbon feed processed, the catalyst utilized in the process, feed contaminants such as hydrogen sulfide, butadiene, oxygenates and other compounds, and the alkylation process reaction conditions. Thus, as the term is more narrowly defined, ASO will be those conjunct polymers produced as a by-product in the catalyzed reaction of mono-olefins with isoparaffins utilizing a catalyst mixture comprising a sulfone component and a hydrogen halide component. The preferred mono-olefins for use in the catalyzed reaction are those having from three to five carbon atoms and the preferred isoparaffins are those having from four to six carbon atoms. The preferred sulfone component is sulfolane and the preferred hydrogen halide component is hydrogen fluoride.

The ASO by-product derived from the hydrocarbon reaction catalyzed by a sulfone-containing alkylation catalyst can be further generally characterized as having a specific gravity, with water at 60° F. as the reference, in the range of from about 0.8 to about 1.0, an average molecular weight in the range of from about 250 to about 350, and a bromine number in the range of from about 40 to about 350.

The hydrogen halide component of the catalyst composition or catalyst mixture utilized in the inventive alkylation process can be selected from the group of compounds consisting of hydrogen fluoride (UF), hydrogen chloride (HC1), hydrogen bromide (HBr), and mixtures of two or more thereof. The preferred hydrogen halide component, however, is hydrogen fluoride, which can be utilized in the catalyst composition in anhydrous form; but, generally, the hydrogen fluoride component utilized can have a small amount of water.

The sulfones suitable for use in this invention are the sulfones of the general formula

wherein R and R' are monovalent hydrocarbon alkyl or aryl substituents, each containing from 1 to 8 carbon atoms. Examples of such substituents include dimethylsulfone, di-n-propylsulfone, diphenylsulfone, ethylmethylsulfone and the alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethyl. enesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen a toms, such as, for example, chloromethylethylsulfone. These sulfones may advantageously be used in the form of mixtures.

When sulfolane is used as the preferred sulfone, it can be utilized in the catalyst composition in anhydrous form, but, more often, the sulfolane component, when added to the catalyst composition as a make-up component, can have a small amount of water. Generally, the sulfolane component used to form the catalyst mixture will have a water concentration up to about 5 weight percent of the total weight of the sulfolane and water. However, preferably, the water contained in the sulfolane component will be in the range of from about 0.1 to about 5.0 weight percent of the total weight of the sulfolane and water and, most preferably, the water will be present in the range of from 0.5 to 4 weight percent.

In the alkylation process, the accumulation of water in the catalyst composition, which comprises hydrogen fluoride and sulfolane, in no event can be more than about 10 weight percent of the total weight of the catalyst composition, which includes sulfolane, hydrogen fluoride and water. Preferably, the concentration of water present in the catalyst is less than about 7.5 weight percent. Most preferably, the concentration of water present in the catalyst is less than 3 weight percent.

Thus, the alkylation catalyst used in the alkylation process wherein an ASO reaction by-product is produced can comprise a hydrogen halide component and a sulfone component, both as described herein, and a concentration ozf water. Preferably, the ASO by-product will. be produced in an alkylation process in which the hydrocarbon mixture is contacted with an alkylation catalyst having sulfolane as its sulfone component and hydrogen fluoride as its hydrogen halide component. In the case where the alkylation catalyst comprises sulfolane and hydrogen fluoride, good alkylation results can be achieved with a weight ratio of hydrogen fluoride to sulfolane in the alkylation catalyst in the range of from about 1:1 to about 40:1. A preferred weight: ratio of hydrogen fluoride to sulfolane can range from about 1.2:1 to about 19:1 and, more preferably, it can range from 1.5: 1 to 9:1.

In order to improve selectivity of the alkylation reaction of the present invention toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized., however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 120° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Contact times for hydrocarbon reactants in an alkylation reaction zone, in the presence of the alkylation catalyst of the present invention generally should be sufficient to provide four essentially complete conversion of olefin reactant in the alkylation zone. Preferably, the contact time is in the range from about 0.05 minute to about 60 minutes. In the alkylation process of the present invention, employing isoparaffin-to-olefin molar ratios in the range of about 2:1 to about 25:1, wherein the alkylation reaction mixture comprises about 40-90 volume percent catalyst phase and about 60-10 volume percent hydrocarbon phase, and wherein good contact of olefin with isoparaffin is maintained in the reaction zone, essentially complete conversion of olefin may be obtained at olefin space velocities in the range of about 0.1 to about 200 volumes olefin per hour per volume catalyst (v/v/hr.). Optimum space velocities will depend upon the type of isoparaffin and olefin reactants utilized, the particular compositions of alkylation catalyst, and the alkylation reaction conditions. Consequently, the preferred contact times are sufficient for providing an olefin space velocity in the range of about 0.1 to about 200 (v/v/hr.) and allowing essentially complete conversion of olefin reactant in the alkylation zone.

In the alkylation process, the reactants can be maintained at sufficient pressures and temperatures to maintain them substantially in the liquid phase and then continuously forced through dispersion devices into the reaction zone. The dispersion devices can be jets, nozzles, porous thimbles and the like. The reactants are subsequently mixed with the catalyst by conventional mixing means such as mechanical agitators or turbulence of the flow system. After a sufficient time, the product can then be continuously separated from the catalyst and withdrawn from the reaction system while the partially spent catalyst is recycled to the reactor. A portion off the catalyst can continuously be regenerated or reactivated as described herein, or by any other suitable treatment, and returned to the alkylation reactor.

One embodiment of the invention herein includes a process which provides for the removal of water which can accumulate in the alkylation catalyst as a result of water introduced into the alkylation system by way of the incoming make-up catalyst components, such as sulfolane and HF, and by way of the hydrocarbon feedstock. The make-up catalyst component can be introduced into the alkylation system as individual components or they can preferably be mixed prior to their introduction into the alkylation catalyst of the alkylation system. The individual sulfoane make-up component generally has a concentration of water often in the range up to about 5 weight percent. Preferably, the water concentration in the individual sulfolane make-up component will be in the range of from about 0.1 to about 5.0 weight percent of the total weight of the sulfolane make-up component and, ,lost preferably, the water will be present in the range of from 0.5 to 4 weight percent.

The sulfolane make-up component can be mixed with the hydrogen fluoride make-up component before introducing the thus mixed components into the alkylation system. It is most desirable for the individual hydrogen fluoride make-up component to be in anhydrous form; but, it can have a small amount of water. Thus, the hydrogen fluoride make-up component can have a water concentration upwardly to about 2 weight percent of the hydrogen fluoride make-up component, preferably, however, the water concentration will be less than about 1 weight percent, most preferably, it can be less than 0.5 weight percent.

The alkylation catalyst of the alkylation process and system is contacted with a hydrocarbon mixture, as described herein, within a reaction zone to thereby produce an alkylate reaction product and an ASO reaction by-product. The reaction product is separated from the alkylation catalyst within a first separation zone to produce a separated reaction product and a separated catalyst mixture with the separated catalyst mixture containing a portion, preferably, a substantial portion, of the reaction by-product. The reaction by-product generally comprises acid soluble oil, which is highly soluble in hydrogen fluoride; and, because of this solubility, a portion, preferably a major portion, of such acid soluble oil, or reaction by-product, will remain in the separated catalyst mixture of the process.

The separated catalyst mixture will have a concentration of water that accumulates within the separated catalyst mixture as a result of make-up catalyst components having water contained therein being introduced, or added, or mixed with the separated catalyst mixture.

Because of the detrimental impact that an excessive water concentration in an alkylation catalyst composition has on the alkylation process or the properties of the resultant alkylate product, it is desirable to minimize the amount of accumulated water in the separated catalyst mixture. Thus, the concentration of water in the separated catalyst mixture can be no greater than about 10 weight percent of the total weight of the separated catalyst mixture which includes sulfolane, hydrogen fluoride and water. Preferably, the concentration of water present in the separated catalyst mixture is less than about 7.5 weight percent. Most preferably, the concentration of water present in the separated catalyst mixture is less than 3 weight percent.

In order to regenerate the separated catalyst mixture by removing at least a portion of the ASO and water that has accumulated therein, a portion of the separated catalyst mixture is passed to a stripping column, which defines a second separation zone, to thereby separate it into st least two streams including a second separation zone overhead stream and a second separation zone bottoms stream. The stripping column can provide means for any suitable separation operation for achieving the objective of the invention; but, preferably, the stripping column is a standard distillation column -that is provided with a feboiler and a overhead system for refluxing. The remaining portion of the separated catalyst mixture not charged to the stripping column can be utilized as a portion of the catalyst mixture of the alkylation reaction zone.

In conventional hydrogen fluoride catalyzed alkylation processes, the stripping of a separated hydrogen fluoride alkylation catalyst is effective for removing water and ASO from the catalyst. In the conventional stripping step., the ASO and water are generally removed by way of a bottoms stream from the stripping column. While the water in a spent conventional hydrogen fluoride alkylation catalyst can adequately be removed by the aforedescribed conventional stripping fractionation methods, these methods in and of themselves are not effective for use when the alkylation catalyst includes, as described herein., an additional sulfolane component. This is because of the azeotropic properties of the components. Thus, with the inventive process described herein, the second separation zone overhead stream will comprise a portion, preferably a substantial portion, of the HF component and a portion, preferably a substantial portion, of the water component of the portion of the separated catalyst mixture charged to the stripping column. As for the second separation zone bottoms stream, it will comprise a portion, preferably a substantial portion, of the sulfolane component and a portion, preferably a substantial portion, of the reaction by-product component of the separated catalyst mixture charged to the stripper column.

Generally, the weight ratio of hydrogen fluoride to water in the second separation overhead stream can range from about 10:1 to about 100: 1; preferably, it can range from about 12:1 to about 200:1, more preferably, it is greater than 24:1. As for the second separation zone bottoms stream, the weight ratio of sulfolane to ASO can be present in the range from about 1.00:1 to about 2:1; preferably, the ratio can range from about 70:1 to about 4:1, and more preferably, the ratio can range from 60:1 to 5:1. Because the stripper is generally not perfectly efficient at making its separations, the second separation zone bottoms stream will often have a small concentration of hydrogen fluoride. The concentration of hydrogen fluoride in the second separation zone bottoms stream in most instances will be less than about 10 weight percent as determined by the weight fraction of the hydrogen fluoride to the total weight of the second separation zone bottoms stream multiplied by a factor of 100. Preferably, the hydrogen halide concentration in the second separation zone bottoms stream is less than about 5 weight percent, and most preferably, the concentration is less than 1 weight percent.

The second separation zone overhead stream is passed to a heat exchanger, which defines a heat transfer zone and provides means for removing heat energy from the second separation zone overhead stream to thereby condense the stream to form a condensed second separation zone overhead stream. A portion of the condensed second separation zone overhead stream can be utilized as a portion of the catalyst mixture, and the remaining portion of-the condensed second separation zone overhead stream can be removed from the alkylation system by passing it to downstream processing. The rate at which the remaining portion of condensed second separation zone overhead stream is removed from the alkylation system is conltrolled so as to effectively maintain a concentration of water in the separated catalyst mixture that is below about 10 weight percent; but, preferably, less than about 7.5 weight percent and, most preferably, less than 3.0 weight percent.

The second separation zone bottoms stream can further be processed to remove a portion, preferably a substantial portion, of the concentration of ASO contained In the second separation zone bottoms stream by passing it to a first contacting vessel which defines a first contacting zone wherein is contained a reversible base. It is genera.]ly desirable to control the flow rate of second separation zone bottoms streams so as to indirectly control the concentration of ASO in the separated catalyst mixture to be maintained at a concentration of no more than about 20 weight percent of the separated catalyst mixture. Preferably the second separation zone bottoms stream flow rate can be such as to maintain an ASO concentration in the separated catalyst mixture of less than about 15 weight percent, and most preferably, the concentration is to be maintained below 10 weight percent.

The second separation zone bottoms stream also contains a portion, preferably a substantial portion, of the sulfolane contained in the feed to the stripping column. Thus, the second separation zone bottoms stream will contain predominantly sulfolane and ASO, but, as earlier described herein, it can have a slight concentration of hydrogen fluoride that has not been recovered in the second separation zone overhead stream. The ASO component in the second separation zone bottoms stream can be present in such concentration levels as earlier described herein.

It is an important aspect of this invention for the contacting of the second separation zone bottoms stream with the contact material or reversible base to result in the removal of at least a portion of the hydrogen fluoride component of the second separation zone bottoms stream to give a neutralized second separation zone bottoms stream having a reduced concentration of hydrogen fluoride below that of the second separation zone bottoms stream. It is preferred, however, to have a significant portion of the hydrogen fluoride component removed from the second separation zone bottoms stream to give a concentration of the hydrogen fluoride component in the neutralized second separation zone bottoms stream of less than about 1.0 weight percent, but preferably, the concentration will be less than about 0.2 weight percent, and most preferably, -the concentration will be less than 0.1 weight percent.

The neutralized second separation zone bottoms stream can also have a reduced concentration of ASO, generally being in the range of from about 2 to about 15 weight percent of the neutralized second separation zone bottoms stream. The concentration of ASO in the neutralized second separation zone bottoms stream, however, will generally be an amount less than about 4 weight percent, and preferably, the ASO will be present in an amount less than 2 weight percent.

The neutralized second separation zone bottoms stream is formed by contacting the second separation zone bottoms stream with a reversible base under conditions suitable for removing a portion of the hydrogen fluoride contained in the second separation zone bottoms stream. The reversible base is preferably selected from the group consisting of poly-(2-vinylpyridine), poly(4-vinylpyridine) and mixtures thereof.

The neutralized second separation zone bottoms stream is further contacted with a carbon adsorbent material contained within a second contacting vessel which defines a second contacting zone and provides means for contacting the neutralized second separation zone bottoms stream with a carbon adsorbent material. The contacting of the neutralized second separation zone bottoms stream with the carbon adsorbent material will remove a portion, preferably a substantial portion, of the ASO contained in the neutralized second separation zone bottoms stream to produce a sulfolane stream substantially free of ASO and hydrogen fluoride. The sulfolane stream can be utilized as at least a portion of the sulfolane component of the alkylation catalyst mixture.

The carbon adsorbent material can be any activated carbon material that is suitable for use as contemplated by this invention and for the selective removal of at least a portion ozf the ASO component contained in the treated sulfone-containing mixture. The activated carbon adsorbent can be characterized by its large specific surface area which can range from about 300 m$^2$/g to about 2500 m$^2$/g as determined by the American Society for Testing Materials (ASTM) Standard Test Method D3663-84 entitled "Standard Test Method for Surface Area of Catalysts". The standard ASTM test D3663-84 is incorporated herein and made a part hereto by reference. Also, the activated carbon adsorbant can further be characterized by its pore diameter which can range from about 1.0 pm to about 50 $\mu$m as determined by the method of mercury intrusion porosimetry described by ASTM Standard Test D4284-88, The ASTM Standard Test D4284-88 is incorporated herein and made a part hereto by reference. It is generally desirable to use commercially available activated carbon. One such suitable commercially available activated carbon, for example, is the product known by its tradename as Calgon Filtrasorb 400, which is manufactured and marketed by Calgon Carbon Corporation.

The process conditions under which the second separation zone bottoms stream and the neutralized second separation zone bottoms stream are contacted with the adsorbent compositions referred to herein can be any conditions that are suitable or effective for removing at least a portion of the concentration of ASO or hydrogen halide, or both, from such sulfolane-containing streams. The removal efficiency of the adsorbent material is not believed to be highly dependent upon the contact pressure because the adsorption phenomenon is thought to be the result of a liquid-solid interaction; however, the process pressure should exceed about 0.5 atmospheres of absolute pressure and can range upwardly to about 30 atmospheres, or more, of absolute pressure. The more common operating pressure will generally range from about atmospheric pressure to about 200 pounds per square inch of gauge pressure (psig).

As for the contacting temperature, any suitable temperature can be utilized that provides for an effective removal of st least a portion of the ASO or hydrogen halide, or both, from sulfolane-containing streams. Generally, the upper and lower temperature limits are set by the physical characteristics of the mixture being treated and the physical characteristics of the ASO contained in such mixture. Considering the lower temperature limit, pure sulfolane has a melting point of about 81.3-82.0° F., but when sulfolane is in the form of a mixture with water and hydrogen fluoride, the melting point is significantly lower. Therefore, the lower limit for the contacting temperature approximates 0° F. As for the upper temperature limit, it is determined by such factors as the initial boiling temperature of the ASO and the temperature at which the sulfone component of the mixture begins to thermally decompose. Thus, the upper contacting temperature approximates 400° F. Therefore, the contact temperature generally will range from about 0° F. to about 400° F. Preferably, the contacting temperature will range from about 50° F. to about 350° F., and most preferably, it will range from 60° F. to 325° F.

When the reversible base becomes spent, it can periodically be regenerated by exposing the reversible base to a suitable solvent under conditions such that at least a portion, preferably a significant portion, of the ASO adsorbed by the reversible base is recovered therefrom. Such suitable solvents can be those solvents in which ASO is soluble and can include organic solvents selected from the group consisting of alcohols, aliphatic hydrocarbons, alkyl halides, amines, aromatic hydrocarbons, esters, glycols, gycol ethers, aroma the halides and mixtures of two or more thereof.

The spent reversible base can also be exposed to a stripping fluid under conditions suitable for removing a substantial portion of the remaining adsorbed ASO not removed by the solvent and to remove at least a portion, preferably, a substantial portion, of the hydrogen fluoride which has been removed from the second separation zone bottoms stream and adsorbed by the reversible base. The stripping fluid can be any fluid which suitably performs the stripping function described herein including, for example, water, hydrocarbons and inert gases. It is desirable for the stripping fluid to be used in the gaseous phase. The hydrocarbons which can suitably be used as a stripping fluid include methane, ethane, propane, butane, pentane, hexane, heptane, octane and mixtures of two or more thereof, but the most preferred stripping hydrocarbon is isobutane.

The conditions under which the reversible base is stripped or exposed to a stripping fluid are such that a regeneration of the reversible base is effected, and it is generally a thermal process whereby the spent reversible base is regenerated by use of thermal energy. Therefore, the stripping temperature is preferably the range of from about 100° F. to about 600° F. When isobutane is used as the stripping fluid, it is preferred for it to be in the supercritical store in order to achieve the best regeneration results. The stripping pressure is not an important aspect of the invention and can range from about; 0.1 to about 140 atmospheres.

When the carbon adsorbent material becomes spent, it can periodically be regenerated by exposing it to a stripping fluid under conditions suitable for removing at least a portion; preferably, a substantial portion of the ASO adsorbed thereon and removed from the neutralized second separation zone bottoms stream. The stripping fluid can be any fluid which suitably performs the stripping function described herein including, for example, water, hydrocarbons and inert gases. It is desirable for the stripping fluid to be used in the gsseoris phase. The hydrocarbons which can suitably be used as a stripping fluid include methane, ethane, propane, butane, pentane, bexane, heptane, octane and mixtures of two or more thereof, but the most preferred stripping hydrocarbon is isobutane which is in a supercritical state.

The conditions under which the carbon adsorbent material is stripped or exposed to a stripping fluid are such that a regeneration of the carbon adsorbent material is effected, and it is generally a thermal process whereby the spent carbon adsorbent material is regenerated by use of thermal energy. Therefore, the stripping temperature is preferably in the range of from about 100° F. to about 600° F. When isobutane is used as the stripping fluid, it is preferred for it to be in the supercritical state in order to achieve the best regeneration results. The stripping pressure is .riot an important aspect of the invention and can range from about 0.1 to about 140 atmospheres, Now referring to FIG. 1, there is depicted by schematic representation an alkylation process system 10. A hydrocarbon fed mixture, comprising olefins and isoparaffins, is introduced into riser-reactor 12 through conduit 14. Riser-reactor 12 defines a reaction zone wherein the hydrocarbon mixture is contacted, or admixed, with a catalyst mixture, comprising sulfolane, water, and hydrogen fluoride, in order to produce a reaction product and a reaction by-product. The olefins of the hydrocarbon feed mixture generally comprise one or more olefins having from three to five carbon atoms, and the isoparaffins of the hydrocarbon feed mixture generally will have from four to six carbon atoms. The catalyst mixture is introduced into riser-reactor 12 via conduit 16.

The admixture of hydrocarbon feed mixture and catalyst mixture passes through the reaction zone defined by riser-reactor 12 wherein a reaction takes place in which the olefins of the hydrocarbon feed mixture react with isoparaffins of the hydrocarbon feed mixture to produce an alkylate reaction product. Also, within the reaction zone, the reaction by-product, ASO, is formed. The reaction effluent, which includes the reaction product and reaction by-product, from riser-reactor 12 passes to settler vessel 18, which defines a separation zone for separating the alkylate reaction product from the catalyst mixture to produce a separated reaction product 20 and a separated catalyst mixture 22. The separated catalyst mixture 22 will contain a portion, but, preferably, a substantial portion, of the alkylation reaction by-product, ASO. The separated reaction product 20 passes to downstream processing via conduit 24. The separated catalyst mixture 22 can be recycled via conduits 26 and 16 to riser-reactor 12 for reuse as the alkylation catalyst mixture. Interposed in conduit 26 is catalyst cooler 28, which defines s heat transfer zone for exchanging heat from separated catalyst mixture 22 to a heat transfer fluid such as water.

A make-up catalyst mixture is introduced into alkylation process system 10 through conduit 30. The make-up catalyst mixture can be prepared by mixing sulfolane, having a concentration of water, with I{F by mixing device 32 which defines a mixing zone and provides means for mixing the sulfolane having a concentration of water with HF to form the make-up catalyst mixture. Hydrogen fluoride is introduced into mixing device 32 via conduit 34, and the sulfolane is introduced into mixing device 32 via conduit 36.

In order to regenerate the alkylation catalyst by :removing accumulated ASO and water, a portion, sometimes referred to as a slip stream or a drag stream, of the separated catalyst mixture 22 passes by way of conduit 37 to stripping column 38 that is equipped with reboiler 39 and which defines a separation zone for separating the slip stream of separated catalyst mixture 22 into at least two streams: (1) an overhead stream, comprising a portion of the hydrogen fluoride contained in the slip stream and a portion of the water contained in the slip stream, and (2) a bottoms stream, comprising a portion of the sulfolane component of the slip stream. The bottoms stream will also contain a portion, preferably a substantial portion, of the reaction by-product, ASO, contained in the slip stream.

Introduced into stripping column 38 by way of conduit 40 is vaporous isobutane which provides energy for separating the slip stream into the overhead stream and the bottoms stream and, more specifically, for stripping the hydrogen fluoride from the slip stream. The overhead stream passes by way of conduit 42 to separator vessel 44. Interposed in conduit 42 is condenser 46, which defines a heat transfer zone and provides means for removing heat energy from the overhead stream and for condensing the overhead stream. The thus-condensed overhead stream passes to separator vessel 44, which defines a separation zone and provides means for separating the thus-condensed overhead stream into an overhead hydrocarbon stream comprising said hydrocarbon, and a condensed overhead stream, comprising F and water. The overhead hydrocarbon stream passes from separator vessel 44 to further downstream processing by way of conduit 48.

A portion of the condensed overhead stream is passed by way of conduit 50 to settler vessel 18 wherein it is recombined with, or utilized as, a portion of the alkylation catalyst mixture. Another portion of the condensed overhead stream is optionally passed to stripping column 38 by way of conduit 51 and is utilized as a reflux to stripping column 38. The remaining portion of the condensed overhead stream not passed to settier vessel 18 or to stripping column 38 is passed by way of conduit 52 to downstream processing. The rate at which the remaining portion of the condensed overhead stream is passed downstream must be controlled so as to be effective in maintaining the concentration of water in the separated catalyst mixture below about 10 weight percent, but preferably, the water concentration is less than about 7.5 weight percent, most preferably, the concentration is less than 3 percent.

The bottoms stream from stripping column 38 passes by way of conduit 54 to first contacting vessel 56, which contains a contact material. Interposed in conduit 54 ]s valve 57 which is utilized along with other piping and valves described herein to assist in isolating first contacting vessel 56. The contact material contained in first contacting vessel 56 is preferably a reversible base and most preferably a polyvinylpyridine (PVP) compound. First contacting vessel 56 defines a separation zone for removing by adsorption or by neutralization, or both, a substantial portion of the hydrogen fluoride contained in the bottoms stream to produce a neutralized bottoms stream or a treated sulfone-containing mixture. Also, at least a portion of the ASO contained in the bottoms stream is adsorbed by the contact material and is thereby removed therefrom.

The neutralized bottoms stream then passes through conduit 58 to second contacting vessel 60, which contains an adsorbent material and defines a separation zone for removing a substantial portion of the ASO contained in the neutralized bottoms stream to produce a regenerated catalyst, or sulfolane stream, having a concentration of ASO that is reduced below that of the neutralized bottoms stream and that is preferably substantially free of ASO and hydrogen fluoride. Interposed in conduit 58 is valve 61 which is utilized along with other piping and valves described herein to assist in isolating second contacting vessel 60. The sulfolane stream conveyed from second contacting vessel 60 passes through conduit 62 to mixing device 32 whereby it is ultimately conveyed and remixed with separated catalyst mixture 22 for reuse as a portion of the sulfolane component of the alkylation catalyst mixture. Interposed in conduit 62 is valve 65 which is utilized along with other piping and valves described herein to assist in isolating second contacting vessel 60. The sulfolane stream can optionally pass by way of conduit 64 to downstream processing.

To regenerate the contact material contained within first contacting vessel 56, conduits 66 and 68, each respectively having valves 70 and 72, are provided to permit the periodic regeneration of the spent contact material. Periodically, the contact material in contacting vessel 56 is exposed to a solvent or a stripping fluid which passes by way of conduit 66 into first contacting vessel 56 to thereby expose the contact material under conditions such that at least a portion of the ASO and HF adsorbed by the contact material is removed by the solvent. The solvent containing ASO and HF which has been removed from the contact material leaves first contacting vessel 56 by way of conduit 68 to downstream processing. To regenerate the contact material contained in second contacting vessel 60, the contact material is exposed to a solvent or a stripping fluid suitable for the removal of at least a portion of the ASO contained upon the contact material. The stripping flaccid is introduced into second contacting vessel 60 by way of conduit 74 to expose the contact material contained therein under conditions so as to regenerate the contact material. The stripping fluid is conveyed from second contacting vessel 60 by way of conduit 76. Interposed in conduits 74 and 76 are, respectively, valves 76 and 78 which are provided to assist in the isolation of second contacting vessel 60.

The following example demonstrates the advantages of the present invention, This example is by way of illustration only, and is not intended to limit the invention as set out in the appended claims.

CALCULATED EXAMPLE

This example provides certain material balance information for an alkylation process unit having a production capacity of 15,000 barrel of alkylate per day. A simplified schematic of the alkylation process unit is depicted in FIG. 1. Table summarizes stream data for the various stream numbers which correspond to those shown in FIG. 1.

TABLE I

| | Stream No. | | | | | | | | | |
|---|---|---|---|---|---|---|---|---|---|---|
| Component/Stream | 14 Reactor HC Feed | 30 Mixed Acid Make-Up | 37 Drag Acid to Rerun | 54 Rerun Bottoms | 52 Rerun OVH Acid Purge | 48 Rerun OVH Hydrocarbons | 40 Stripping IC$_4$ to Rerun | 50 Rerun OVH Acid | Rerun OVH HF Recycle | 26 Acid from Settler |
| Ethane | — | — | — | — | — | — | — | — | — | — |
| Propylene | 0.45 | — | — | — | — | — | — | — | — | — |
| Propane | 19.53 | — | — | — | — | 0.30 | 0.30 | — | — | — |
| Isobutane | 2,745.21 | — | — | — | — | 58.17 | 58.17 | — | — | — |
| Butene | 210.09 | — | — | — | — | — | — | — | — | — |
| N-Butene | 273.05 | — | — | — | — | 4.44 | 4.44 | — | — | — |
| Isopentane | 49.25 | — | — | — | — | 0.02 | 0.02 | — | — | — |
| Pentane | — | — | — | — | — | — | — | — | — | — |
| Amylenes | — | — | — | — | — | — | — | — | — | — |
| C$_6$+ | — | — | — | — | — | — | — | — | — | — |
| Total HC | 3,297.59 | — | — | — | — | 62.93 | 62.93 | — | — | — |
| HF | 15.01 | 0.1440 | 21.35 | 0.21 | 0.1418 | 0.38 | 0.10 | 20.85 | 20.71 | 13,205.90 |
| Sulfolane | — | 0.2835 | 10.10 | 10.10 | — | — | — | — | — | 6,250.16 |
| ASO | — | — | 0.76 | 0.76 | — | — | — | — | — | 470.96 |
| H$_2$O | 0.17 | 0.0037 | 0.67 | — | 0.0046 | — | — | 0.67 | 0.67 | 415.28 |
| Total - Gal/min | 3,312.77 | 0.4312 | 32.88 | 11.07 | 0.1463 | 63.31 | 63.03 | 21.52 | 21.37 | 20,343.30 |
| Total - lbs/hr | 945,410 | 251 | 17,308 | 6,900 | 70 | 17,923 | 17,787 | 10,272 | 10,202 | 10,709,784 |
| Flowing Conditions | | | | | | | | | | |
| Temperature, F. | 104 | 100 | 290 | 360 | 55 | 55 | 375 | 55 | 55 | 102 |
| Pressure, psia | 200 | 120 | 75 | 70 | 65 | 65 | 70 | 65 | 65 | 75 |

While this invention has been described in terms of the presently preferred embodiment, reasonable variations and modifications are possible by those skilled in the art. Such variations and modifications are within the scope of the described invention and the appended claims.

That which is claimed is:

1. An alkylation process, comprising the steps of:
   (a) mixing sulfolane having a concentration of water with HF to form a catalyst mixture comprising sulfone, water and HF;
   (b) contacting a hydrocarbon mixture, comprising olefins and isoparaffins, with said catalyst mixture within a reaction zone to thereby produce a reaction product and a reaction by-product;

(c) separating said reaction product from said catalyst mixture within a first separation zone to produce a separated reaction product and a separated catalyst mixture with said separated catalyst mixture containing a portion of said reaction by-product;

(d) passing a portion of said separated catalyst mixture to a second separation zone to thereby separate said portion of said separated catalyst mixture into a second separation zone overhead stream, comprising a portion of the HF component of said portion of said separated catalyst mixture and a portion of the water component of said portion of said separated catalyst mixture, and a second separation zone bottoms stream, comprising a portion of the sulfolane component of said portion of said separated catalyst mixture and a portion of the reaction by-product component of said portion of said separated catalyst mixture;

(e) utilizing a remaining portion of said separated catalyst mixture as a portion of said catalyst mixture;

(f) condensing said second separation zone overhead stream to produce a condensed second separation zone overhead stream;

(g) utilizing a portion of said condensed second separation zone overhead stream as a portion of said catalyst mixture; and (h) passing a remaining portion of said condensed second separation zone overhead stream to downstream processing at a rate which is effective in maintaining a concentration of water in said separated catalyst mixture below about 10 weight percent.

2. A process as recited in claim 1, wherein the concentration of water in said sulfolane used in mixing step (a) is in the range of from about 0.1 to about 5 weight percent.

3. A process as recited in claim 2, wherein the weight ratio of hydrogen fluoride to sulfolane of said catalyst mixture is maintained in the range of from about 1.1 to about. 40:1 weight percent.

4. A process as recited in claim 3, wherein in said second separation zone overhead stream the weight ratio of tIF to water is in the range of from about 1.01 to about 100: 1.

5. An alkylation process as recited in claim 4, further comprising:

passing said second separation zone bottoms stream to a first contacting zone at a rate which is effective in maintaining a concentration of said reaction by-product in said separated catalyst mixture of less than about 20 weight: percent of said separated catalyst mixture.

6. An alkylation process as recited in claim 5, further comprising:

introducing a hydrocarbon in a vaporous state into said second separation zone to thereby prey:[do energy for separating said portion of said separated catalyst mixture into said second separation zone overhead stream and said second separation zone bottoms stream; and separating said condensed second separation zone overhead stream into an overhead hydrocarbon stream, said overhead hydrocarbon stream comprising said hydrocarbon, and said condensed second separation overhead stream, said condensed second separation overhead stream comprising HF and water.

7. A process as recited in claim 6, further comprising:

contacting said second separation zone bottoms stream with a reversible base selected from the group consisting of poly-(2-vinylpyridine), poly-(4-vinylpyridine), and mixtures thereof contained within said first contacting zone to thereby remove a portion of the HF contained in said second separation zone bottoms streams to produce a neutralized second separation zone bottoms stream;

contacting said neutralized second separation zone bottoms stream with carbon contained within a second contacting zone to thereby remove a portion of said portion of the reaction by-product to produce a sulfolane stream substantially free of said reaction by-product: and HF; and utilizing said sulfolane stream as at least a portion of the sulfolane component of said catalyst mixture.

8. An alkylation :process as recited in claim 7, further comprising:

periodically exposing said reversible base to a solvent under conditions such that at least a portion of the acid soluble oil adsorbed by said reversible base is removed therefrom.

* * * * *

UNITED STATES PATENT AND TRADEMARK OFFICE
CERTIFICATE OF CORRECTION

PATENT NO. : 5,347,065

DATED : September 13, 1994

INVENTOR(S) : Richard L. Anderson

It is certified that error appears in the above-indentified patent and that said Letters Patent is hereby corrected as shown below:

Column 15, claim 4, line 46, delete "tlF" and insert --- HF --- therefor.

Column 16, claim 5, line 7, delete ":" after "weight".

Column 16, claim 6, line 12, delete "prey:[do" and insert --- provide --- therefor.

Column 16, claim 7, line 38, delete ":" after "product".

Column 16, claim 8, line 41, delete ":" before "process".

Signed and Sealed this

Twentieth Day of December, 1994

Attest:

BRUCE LEHMAN

*Attesting Officer*        *Commissioner of Patents and Trademarks*